United States Patent [19]

Finn

[11] Patent Number: 5,407,809
[45] Date of Patent: Apr. 18, 1995

[54] DIGESTER FOR CONVERTING ORGANIC MATERIAL INTO COMPOST

[75] Inventor: Larry J. Finn, Gladewater, Tex.

[73] Assignee: Bedminster Bioconversion Corporation, Cherry Hill, N.J.

[21] Appl. No.: 72,905

[22] Filed: Jun. 7, 1993

[51] Int. Cl.⁶ ............................................. C12M 1/10
[52] U.S. Cl. .................................... 435/41; 34/137; 71/9; 366/228; 422/184; 435/299; 435/312; 435/313
[58] Field of Search ............... 435/299, 312, 313, 303, 435/309, 41, 262; 422/184, 209, 233; 34/137, 135, 599, 602; 71/9; 366/220, 225, 228

[56] References Cited

U.S. PATENT DOCUMENTS

| | | | |
|---|---|---|---|
| 1,518,938 | 12/1924 | Nielsen | 34/137 |
| 2,187,601 | 1/1940 | Glaxner | 134/60 |
| 2,660,807 | 12/1953 | Walsh | 34/136 |
| 2,686,754 | 8/1954 | Monod | 195/143 |
| 2,787,599 | 4/1957 | Belden | 422/209 |
| 3,021,202 | 2/1962 | Peirce | 23/286 |
| 3,028,314 | 4/1962 | Means | 195/141 |
| 3,054,663 | 9/1962 | Komline | 366/228 |
| 3,064,948 | 11/1962 | Hallberg | 259/3 |
| 3,138,447 | 6/1964 | Eweson | 71/9 |
| 3,149,922 | 9/1964 | Lavallee | 23/259.1 |
| 3,178,267 | 4/1965 | Larson | 422/233 |
| 3,216,345 | 11/1965 | Rigby et al. | 366/225 |
| 3,297,410 | 1/1967 | De Lisle | 422/209 |
| 3,419,250 | 12/1968 | Brennan | 259/41 |
| 3,588,052 | 6/1971 | Scholtz | 259/3 |
| 3,595,534 | 7/1971 | Burton | 366/225 |
| 3,666,240 | 5/1972 | Lodige et al. | 366/228 |
| 3,676,074 | 7/1972 | Shibayama et al. | 435/312 |
| 4,043,886 | 8/1977 | Bierker et al. | 422/186 |
| 4,169,878 | 10/1979 | Etherington | 422/184 |
| 4,177,575 | 12/1979 | Brooks | 34/13 |
| 4,342,836 | 8/1982 | Harvey | 435/316 |
| 4,365,974 | 12/1982 | Elmore | 48/111 |
| 4,606,647 | 8/1986 | Frye | 366/150 |
| 4,729,877 | 3/1988 | Hennig | 422/134 |
| 4,738,930 | 4/1988 | Faltejsek | 435/306 |
| 4,836,918 | 6/1989 | Szikriszt | 435/312 |
| 5,047,349 | 9/1991 | Eweson | 435/312 |
| 5,206,173 | 4/1993 | Finn | 435/313 |

FOREIGN PATENT DOCUMENTS 17975 of 1904 United Kingdom .

Primary Examiner—James C. Housel
Assistant Examiner—Jan M. Ludlow
Attorney, Agent, or Firm—Stanley H. Zeyher

[57] ABSTRACT

A rotatable digester drum for convening organic waste material into compost which has internally disposed along its longitudinal axis a series of spaced-apart baffles, each baffle having a variable cross sectional area ranging from 60 to 100% of the cross sectional area of the drum and arranged with respect to one another when in the partially open mode to cause material and air introduced into the drum to traverse a non-linear path through the drum, the drum having a plurality of longitudinally extending internal ribs arranged in spaced array around its circumference.

5 Claims, 5 Drawing Sheets

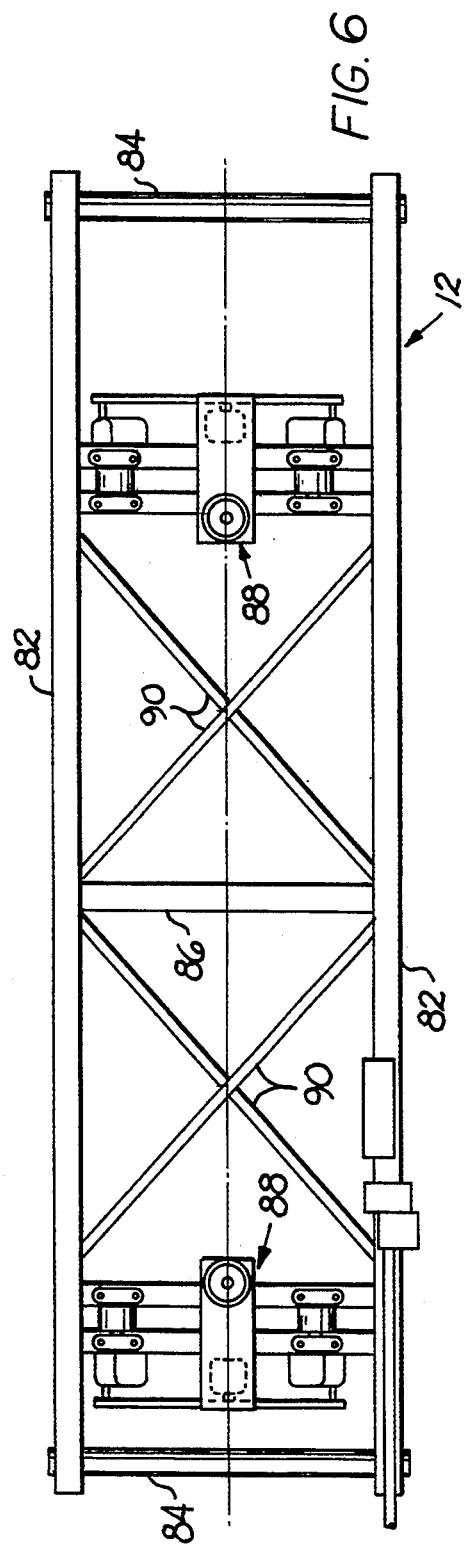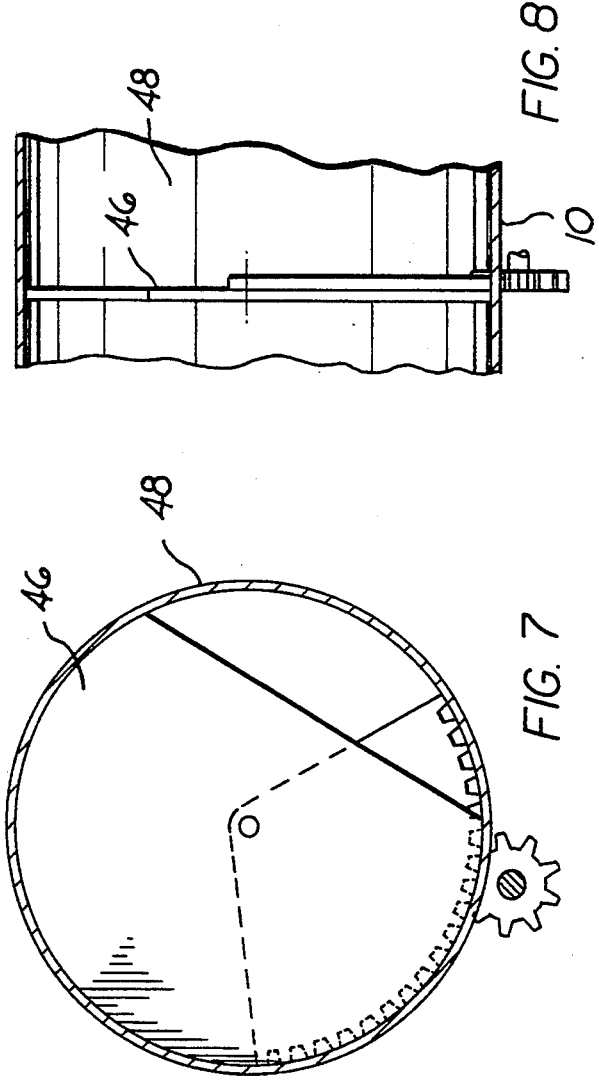

DIGESTER FOR CONVERTING ORGANIC MATERIAL INTO COMPOST

BACKGROUND OF THE INVENTION

This invention relates broadly to a process and apparatus for the biological degradation of organic waste material into compost and more particularly to a process and apparatus for the microbial treatment of waste streams of essentially organic composition uncontaminated by inorganic materials. For optimum performance of the process it is important that material undergoing treatment be organically degradable, substantially uniform in composition and finely comminuted.

Farm waste, for example, meets the requirement of substantial uniformity in composition as do waste streams generated by fast-food chains, restaurants and other waste generating activities of more or less predictable nature. To achieve the degree of comminution thereby to accelerate the biological process the material is shredded prior to being introduced into the digester drum.

It should also be noted that the process and apparatus of this invention can also be utilized in the treatment of municipal solid waste when undesirable inorganic components of the waste stream are removed by presorting and the organic material itself is properly sized by first being passed through a shredder or other suitable mechanism before being introduced into the digester chamber.

By limiting the composting process to the treatment of waste material meeting the above qualifications a unique continuous feed digester of reduced size, cost and complexity can be employed as contrasted with the large size, relatively costly batch-treatment systems of the prior art as exemplified by U.S. Pat. Nos. 5,047,349 and 3,245,759 assigned to the assignee of the present invention.

It should be noted, for example, that present day techniques for handling farm waste are to windrow the material or to spread the raw organic material on the land. The former technique is both time consuming and an inefficient use of land and the latter technique is one coming under increasing scrutiny and regulation by the EPA as an environmentally unsound and possibly hazardous practice in that run off of such material into streams, ground water, and aquafirs could result in contamination of the potable water supply.

The present invention addresses these problems by providing an economic and expeditious process and apparatus for converting organic waste streams such as described above into a rich humus or compost which after treatment meets the vector attraction and pathogen reduction requirements of a class one product as currently defined by the EPA.

SUMMARY OF THE INVENTION

In accordance with apparatus aspects of the present invention there is provided a digester for the bio-degradation of natural organic material by treating with aerobic micro organisms which comprises a digester drum of circular cross sectional configuration mounted on an inclined plane for rotation about its longitudinal axis. In contrast to prior art devices utilizing isolated and staged treatment zones such, for example, as taught in U.S. Pat. No. 5,047,349, the drum has disposed internally along it length, at spaced intervals transverse its longitudinal axis, a series of partially obstructing baffles each occupying from 60-70 percent of the cross-sectional area of the drum. The baffles are arranged with respect to one another so that air forced into and thru the drum as well as material undergoing treatment within the drum is caused to traverse a more or less sinusoidal or serpentine path. By such an arrangement material undergoing treatment within the rotating drum is fully aerated as it tumbles and is dispersed through the air stream. To facilitate movement of the material through the rotating drum it is inclined from the horizontal. Material to be treated is fed in at one end through a transfer box of the type shown and claimed in U.S. Pat. No. 5,047,349, the teaching of which is hereby incorporated by reference. Material is removed from the opposite end, as required, through slideable doors provided in the downstream end of the drum surface. Air is blown through the digester in counter flow relation to movement of material through the drum.

The internal surface of the drum is uniquely provided with a series of circumferentially spaced ribs extending longitudinally along the drum inner surface. These ribs serve a multiplicity of functions; as innoculant retention means, thereby to insure proper bacterial seeding of successive drum loadings and structural strengtheners of the drum along its longitudinal axis, and after deposit of treated material within the interstices formed between adjacent ribs, as corrosion inhibitors and as a means of providing thermal insulation.

A still further feature of the invention, is the provision of means for adjusting the path and flow rate of both air and material traversing the digester drum by varying the size and disposition of the baffle openings.

Another unique feature of the invention is the portability and inexpensive operational set-up of the digester. This permits it use at various work sites dependent on need. One contemplated use of such equipment is its installation at different farm and fast-food locations for treatment of waste without costly preconditioning of the site.

BRIEF DESCRIPTION OF DRAWINGS

The foregoing and other important aspects of the invention will be more apparent from the following disclosure and by reference to the following drawings. For the purpose of illustrating the invention, there is shown in the drawings a form which is presently preferred; it being understood, however, that this invention is not limited to the precise arrangements and instrumentalities shown.

Referring now more particularly to the drawings:

FIG. 6 is a plan view of the skid;

FIG. 7 illustrates one form of mechanism for varying the baffle openings; and

FIG. 8 is a side view of the baffle adjusting mechanism.

The same reference numerals are used throughout the drawings to designate the same or similar parts.

DETAIL DESCRIPTION OF THE PRESENTLY PREFERRED EMBODIMENTS

Figure 1:
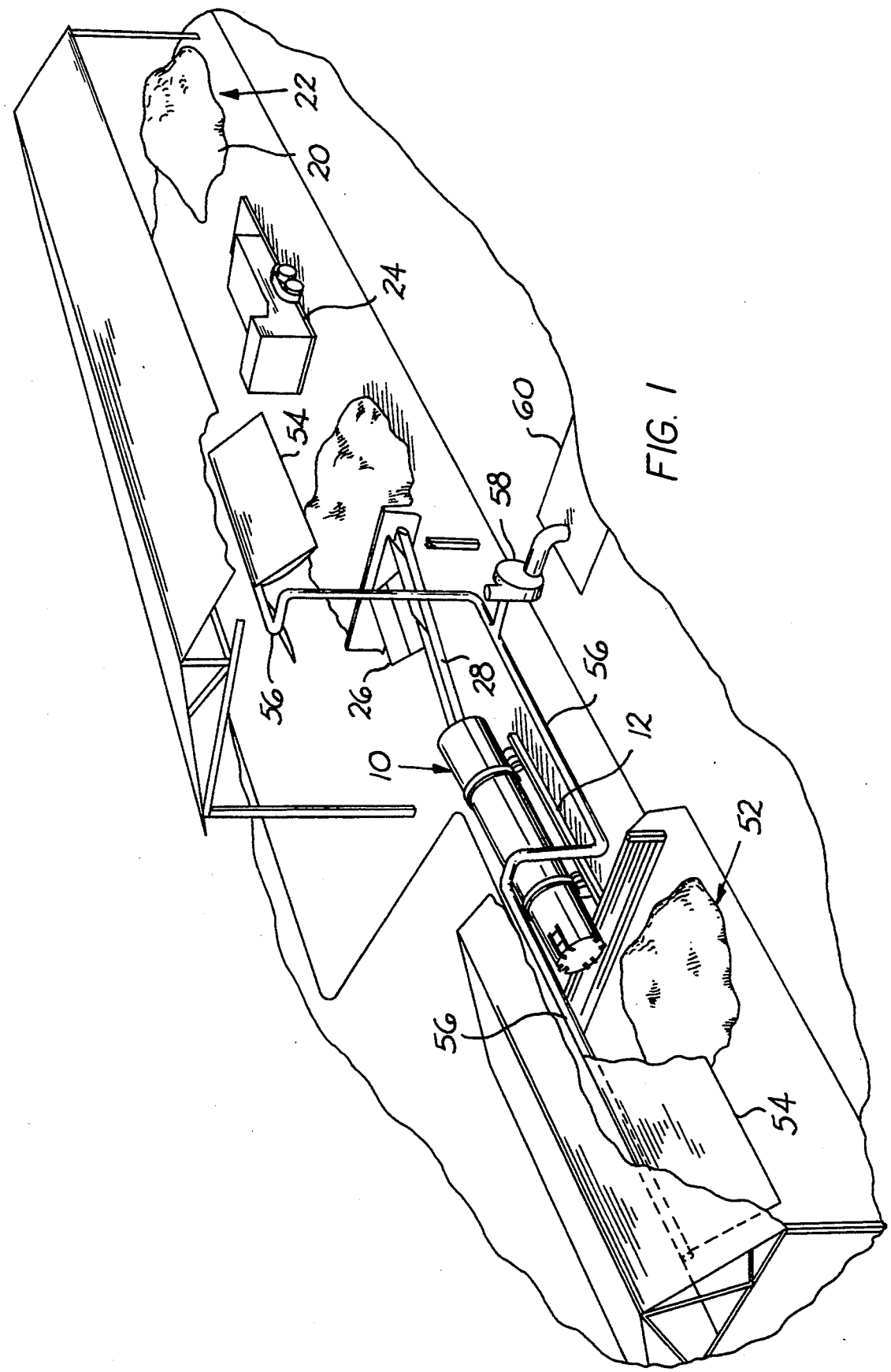
FIG. 1 is a perspective showing of a facility incorporating the subject digester.

Referring to FIG. 1 of the drawing there is shown a facility for converting source-separated municipal solid waste into compost utilizing a digester comprising a drum 10 mounted on skid 12 and adapted for rotation about its longitudinal axis 14. The axis of the drum is inclined from the horizontal to facilitate gravity feed of material through the drum from the higher elevation to the lower elevation as the drum rotates. Details for mounting and rotating the drum, as well as for supplying forced air to the drum can best be understood by referring to FIGS. 2 and 3.

Figure 2:
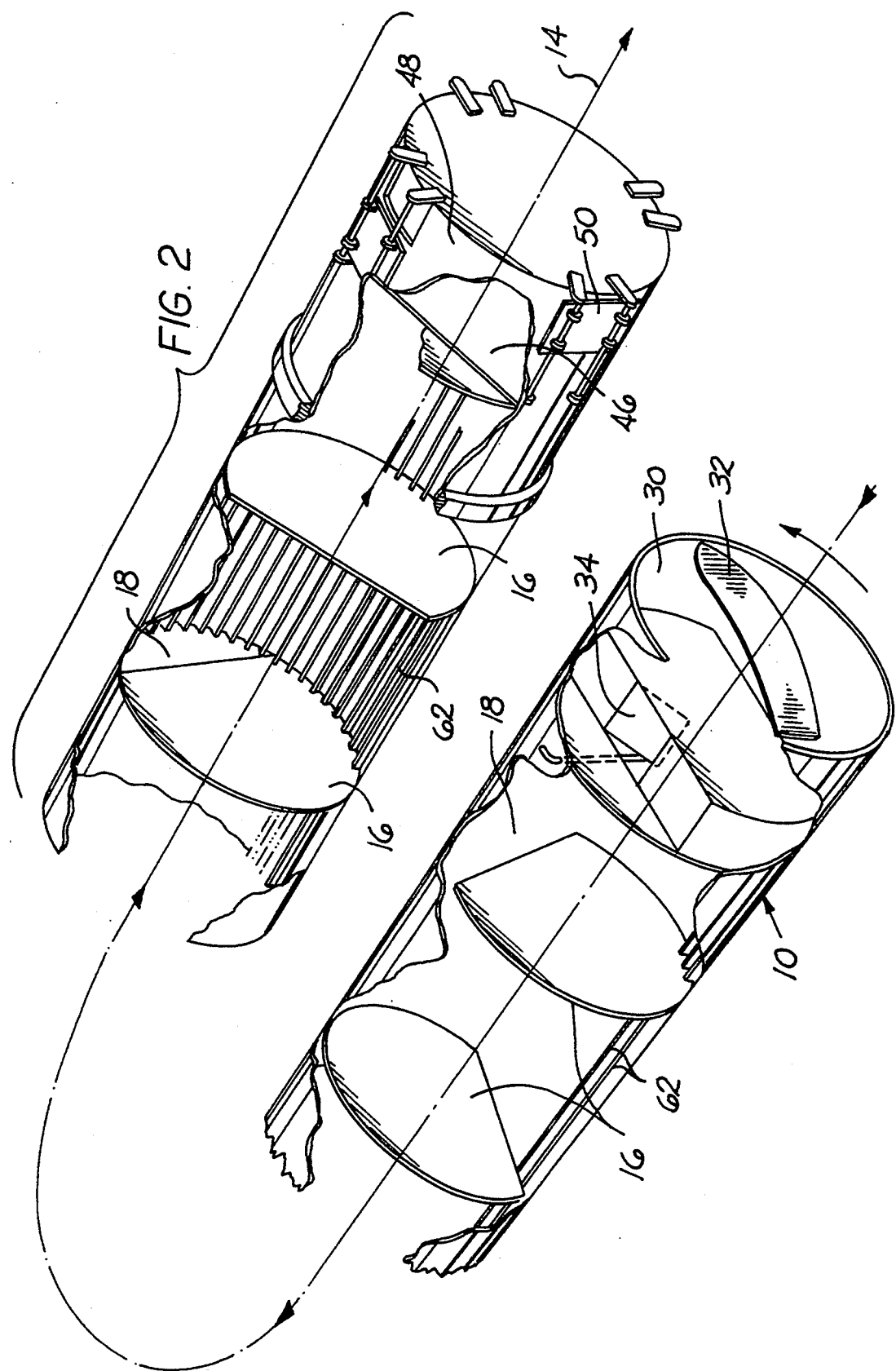
FIG. 2 is a cutaway perspective of the digester illustrating its internal construction.

As shown in the drawings the drum 10 has a plurality of spaced-apart, partially obstructing baffles 16 positioned along the length of the drum in a direction transverse the longitudinal axis 14 of the drum. Each of the baffles 16, as seen in FIG. 2, is truncated to provide an opening 18 to permit movement of material through the drum and for controlling the direction of air flow through material undergoing treatment within the drum.

Incoming waste material 20 is pre-sorted to insure that it contains no undesirable inorganics or oversized materials. The waste material is stockpiled at position 22 from where it is fed into a shredder 24 to effect its comminution into particulate matter of predetermined size. This step greatly increases the surface area of the material exposed to microbial treatment within the digester and materially expedites the ensuing metabolic process. Material so treated is then dumped into a feed hopper 26 positioned over an inclined feed conveyor 28 which transports the comminuted waste material into the feed box 30 of digester drum 10 (See FIG. 2). The feed box is provided with a series of one quarter inch thick stainless steel scoop plates 32 having the configuration shown in FIG. 2. The scoop plates effectively shovel the waste material into transfer boxes 34. The transfer boxes 34 are gravitationally operable and have the construction disclosed in U.S. Pat. No. 5,047,349. The transfer boxes are arranged to operate by gravity and digester rotation alone. This mode of operation is effected through hinged transfer doors 36. The doors close when at the bottom of the drum as seen at 38 in FIG. 3 and open when at the top of the drum as seen at 40 in FIG. 3. Material enclosed within the transfer box is dumped into the treatment zone 42 of the drum as the transfer box reaches its top position within the drum. As the inclined drum rotates the material is caused to tumble as it traverses the length of the drum. Ports 43 provide access to the inside of the drum to facilitate observation of the process and sampling of material. As material is moved through the drum air is blown through port 44 in the downstream end of the drum in counterflow relation to the movement of material through the drum. Because of the unique positioning of the openings provided by the baffle truncations air traversing the drum is caused a flow in a generally sinusoidal pattern and thus through the material fully aerating material tumbling in its path. To provide the desired circuitous path for air flow through the drum the baffle openings are radially spaced from one another 120 to 180 degrees apart. The truncations provide openings which equal from 30-40% of the cross-sectional area of the drum. As the drum rotates the material being processed within the drum undergoes decomposition as a result of the various strains of aerobic bacteria colonizing the drum which act on the finely comminuted waste material in its passage through the drum. At the discharge end of the drum an adjustable baffle 46 is provided to permit the desired degree of filling of the discharge box 48 or if desired to close it off completely from the rest of the system. Composted material can be withdrawn from the outlet box through slideable discharge doors 50. Material discharge from the digester is deposited in the compost loading area 52.

To control ordors, generated by the system both the feed and discharge areas are covered by an ordor-control hood 54 and an exhaust duct system 56 of the type shown and described in U.S. Pat. No. 5,206,173, assigned to the assignee the subject invention the teaching of which is hereby incorporated by reference. The hood is shaped so that process air emanating from the pile contacts the under surface of the hood while ambient outside cool air is caused to traverse the upper surface of the hood. As a result of this heat exchange arrangement process air is dehumidified while concomitantly the ambient air is heated. The hood is pitched to cause condensate to run down its surface and not to drip. Warm ambient air is used to heat the composting facility and dehumidified process air and condensate can be reused in the composting process. Ordor emanating from these areas is drawn off by the exhaust air fan 58 and passed through a soil filter 60 before release to the atmosphere.

As mentioned above a feature of the invention is the treatment of the inner wall surface of the drum. The inner surface of the drum is provided with a series of ribs 62 arrayed around the entire inner circumference of the drum on 6 inch centers, each rib is one half inch thick and two inches high and extends along the entire length of the treatment zone of the drum. In the above illustration the ribs are made of hot rolled flat bar steel spot welded to the drum surface. As previously noted the ribs serve a plurality of functions: they act as drum strengtheners, innoculant retention means, and corrosion inhibitors. As composted material builds up within the interstices formed by adjacent ribs, the material acts as both an insulator and protects the inner surface of the drum from the highly corrosive effects of the material undergoing treatment and the acids generated as a result of the bacterial metabolic process. Because of the temperature-insulating effect of the material deposited between the ribs the external insulation required to maintain proper operating temperatures within the drum can be reduced. Additionally the thickness of the drum wall can be reduced without effecting its wearability life as well as providing a lighter overall system.

The rate at which treated material is deposited in the discharge chamber of the drum can be controlled through use of an adjustable baffle 46 and if desired the discharge area 48 can be completely isolated from the treatment zone 42. One form of mechanism for varying the baffle openings is illustrated in FIGS. 7 and 8. Similarly the size of the various baffle openings can be adjusted in this manner and if desired the illustrated continuous feed system can be converted to a staged batch system through the opening and closing of the variable baffles to effect transfer of material from one staging area to the next. The transfer of material through the treatment zone can thus be regulated. More importantly the closing off of selected sections of the treatment zone by use of such baffles permits processing of unground municipal solid waste without the need for transfer doors and boxes such as used in the system described in U.S. Pat. No. 5,047,349. By the simple expedient of using baffles having adjustable openings the continuous feed operation of the present invention can be transformed into a batch process of the type described in the above-mentioned patent. By converting the drum into one or more distinct stages partial emptying of the drum can be effected to avoid a phenomenon known as rag and film plastic balling which often occurs in the treatment of unsorted and unground municipal solid waste. Accordingly it will be appreciated that a continuous feed system as shown and described in the present invention can through use of such baffles be convened to a batch process not requiring source-separate or pre treated waste. This eliminates the need for a costly and somewhat complex in-drum transfer system. It also should be noted that the ability to close off sections of the system at will permits isolating an area in which balls exist thereby permitting their removal through discharge doors 50 without shutting down the entire system.

Figure 3:
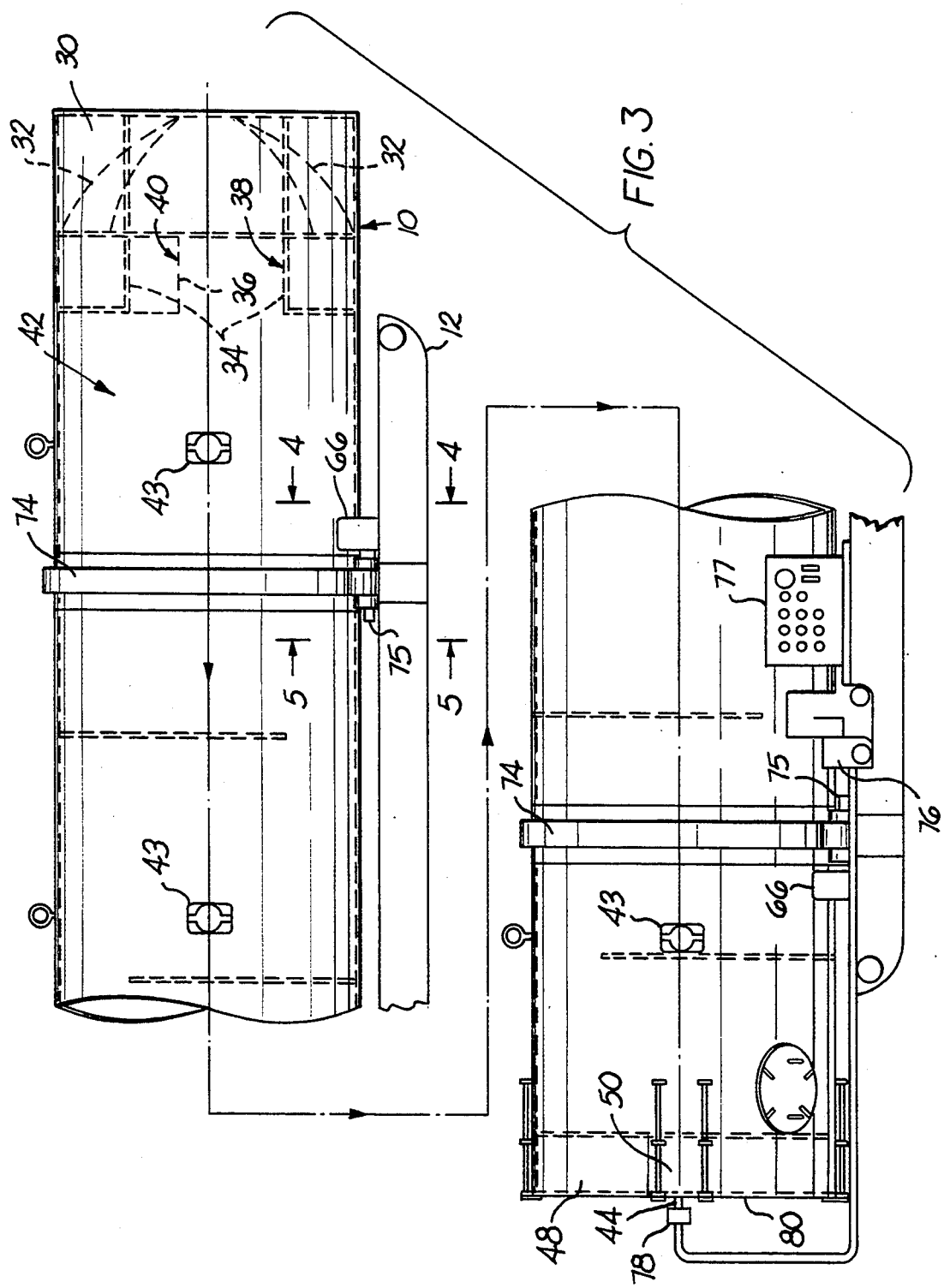
FIG. 3 illustrates the diester-skid assembly.
Figure 4:
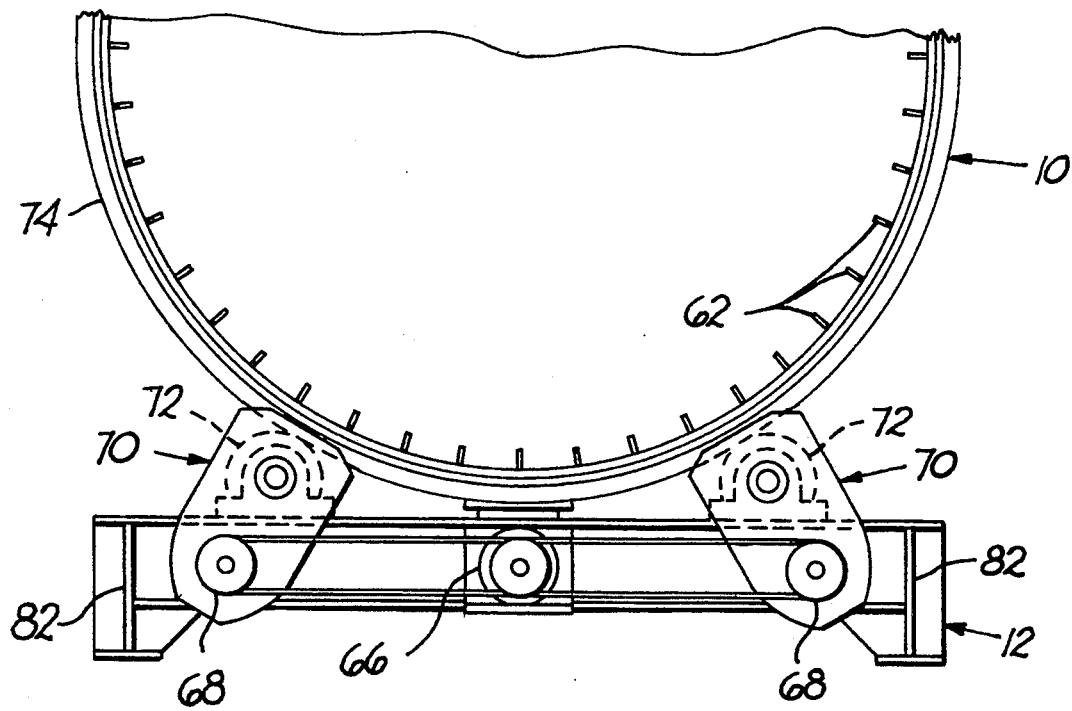
FIG. 4 is a cross sectional view of the digester-skid assembly taken along the cutting plane 4—4.
Figure 5:
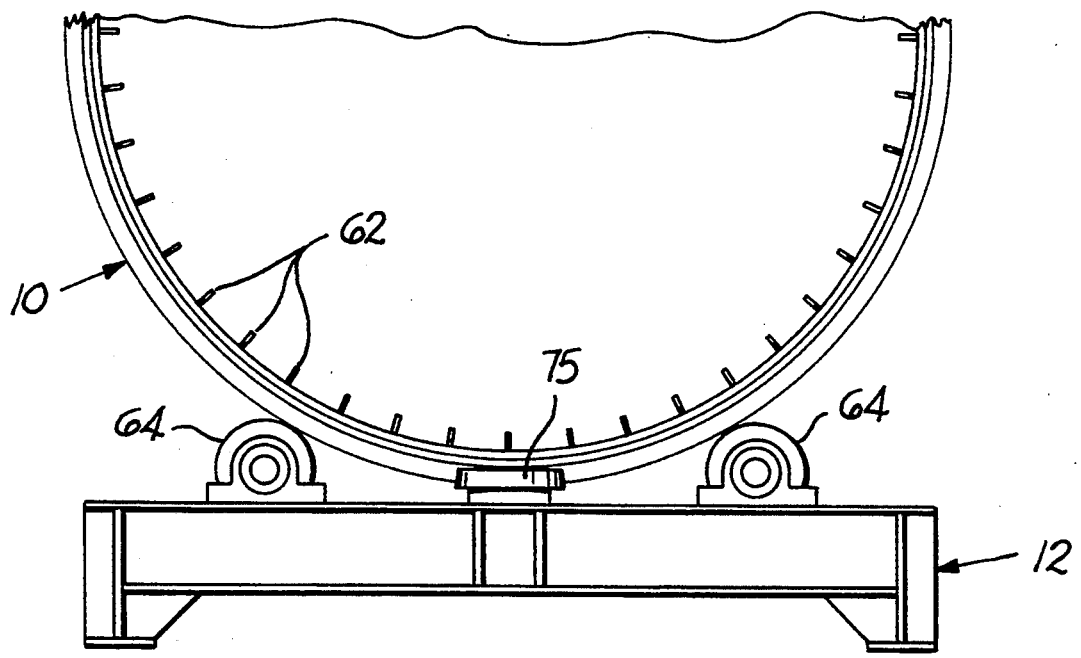
FIG. 5 is a cross sectional view of the digester-skid assembly taken along the cutting plane 5—5.

The illustrated digester drum is made of one quarter inch SA 36 steel plate, with an overall length of 40 feet and an outside diameter of 95 inches. It should be understood, that all dimensions, given by way of example, are subject to change with capacity changes. To insure proper operating temperature within the drum of between 35–75 degrees Celsius, it is overlaid with a urethane foam coating 1 to 2 inches thick. The overall dimensions of the digester permit its highway transport. As seen in FIGS. 4 and 5 the drum is supported on adjustable trunnions 64 and is rotatably driven by a pair of 5 hp, 1750 rpm electric motors 66. The motors are belt coupled to sheaves 68 which acting through a 228.50:1 speed reducing gear trains, contained within assemblies 70 drive the rollers 72 at 6.28 rpm. The gear reducing unit 70 as seen in FIG. 4 is positioned 16 degrees off the vertical and tensioned so as to bring the rollers 72 into friction bearing relation with the six inch wide face of tires 74 shrunk-fit to the drum surface around its entire circumference. The tires are made of 4140 high temperature steel having a hardness number of between 33 and 38 RC. To prevent sideways movement of the drum, thrust rollers 75 are positioned to bear on confronting surfaces of tires 74, as best seen in FIG. 3 and 5.

The mechanical, electrical and pneumatic requirements for operating the digester are carried by skid 12. By this novel arrangement, the unit, once in place, can be activated through a single electrical hookup. The skid mounts a roots universal rotary positive blower 76 capable of producing a maximum rate of airflow equal to three times the volume of the drum vessel each hour. Air is introduced into the drum by means of rotary slip coupling 78 connecting the output of the blower to a standard pipe 44 threaderably secured to the drum end plate 80. During treatment of waste within the drum, air is pumped in counter-flow relation to the movement of material through the drum. This reverse process airflow utilizes waste heat from material at the discharge end to heat incoming feed stock. It also advantageously concentrates $CO_2$ at the feed end to promote carbonic acid formation for accelerated degradation of in-feed material. As previously noted, the truncated baffles provide a serpentine flow of air through the digester. This causes air to flow through the entrained mass in a direction defined by the free space provided in the baffle above the mass, thereby insuring an aerobic process and maintaining the mass temperature in the 35 to 75 Celsius degree range To provide proper operating temperatures within this range, the drum is overlaid with a urethane foam coating 1 to 2 inches thick. To permit hookup to external power an electrical control box 77 is provided.

As seen in FIG. 6 support frame or skid 12 on which the digester drum 10 is mounted is constructed of two 30 foot long steel I beams 82 spaced 90 inches apart. Welded transverse the length of the I beams at either end thereof are 8 inch diameter standard steel pipes 84. Welded to the I beam side supports at a position intermediate the two digester bearing support structures 88 is an I beam cross member 86. Additional structural rigidity is obtained by means of one quarter inch thick steel L-shaped bracing members 90 three inches on a side secured to side supports 82.

It should be understood that the subject invention has a number of apparatus and methodology aspects. The digester per se is unique in its provision of a continuous feed system employing spaced, partially obstructing baffles arrayed in a staggered relation so as to provide a serpentine path for movement of air and waste material through the drum during its microbial treatment within the drum. To accelerate the conversion of organic waste material into compost the material is first sized by being passed through a shredder and associated gratings to produce particle sizes of between ½ to 11/2 inches. An additional feature of the invention is the provision of longitudinally extending ribs disposed around the circumference of the drum. These features taken in combination with those previously described produce a unique system and method for the treatment of source-separated municipal and farm waste.

It will be appreciated that the present invention may be embodied in other specific forms than those illustrated and described herein without departing from the spirit or essential attributes thereof and, accordingly, reference should be made to the appended claims, rather than to the foregoing specification as indicating the scope of the invention.

I claim:

1. In a system for converting organic waste material into compost, the combination comprising:
    a shredder for comminuting waste into particulate matter of predetermined size; a cylindrical drum; means for rotating said drum about its longitudinal axis, said drum having a feed box at one end thereof for receiving material to be processed and an annulus-fronted discharge chamber at the opposite end thereof for receiving treated material; a treatment zone intermediate said feed box and discharge chamber and transfer boxes for conveying material from said feed box to said treatment zone, and said treatment zone containing a series of baffles each occupying approximately between 60 to 70% of the cross sectional area of the drum disposed in spaced relation along said axis perpendicular thereto;
    means for loading comminuted waste into said feed box and said feed box having scoop plates mounted on its internal surface for moving waste material into said transfer boxes;
    means for forcing air through said treatment zone in counter-flow relation to the movement of material through said drum and said drum having, arrayed around the entire inner circumference of the drum and extending the length of the treatment zone, a series of ribs having entrapped between adjacent ribs waste material undergoing composting thereby to retain inoculant and to insulate the drum surface from heat loss and the corrosive effects of the composting process and said ribs further providing drum strengthening;

means inclining the drum to the horizontal and for rotating the drum to cause movement of material through the treatment zone for deposit into said discharge chamber; and means for removing treated material from the discharge chamber.

2. A digester for converting organic waste material into compost comprising:

a cylindrical drum; means for rotating the drum about its longitudinal axis; a plurality of baffles disposed internally of the drum in spaced relation perpendicular to the longitudinal axis of the drum each baffle having an opening at one end thereof and having a cross-sectional area 30-40% less than the internal cross sectional area of the drum and said openings collectively defining an uninterrupted serpentine path, through which material and air introduced into the drum are constrained to follow;

means for introducing waste material into the drum at one end thereof and a port at the opposite end thereof for discharging material; means for introducing air into said drum at said opposite end in counter-flow relation to the movement of material through the drum; and said drum having arrayed around its inner circumference longitudinally extending ribs entrapping waste material undergoing composting thereby to retain inoculant and to insulate the drum from heat loss and the corrosive effects of the composting process.

3. The method of converting organic waste material into compost, which comprises:

introducing organic waste material into a horizontally-disposed rotating drum having an inside diameter of at least approximately 8 feet and a length of at least approximately 5 times its diameter; a plurality of baffles being provided within said drum in spaced relation along and perpendicular to the longitudinal axis of the drum, each baffle having an adjustable cross-sectional area ranging from approximately 60 to 70% of the cross-sectional area of the drum;

the openings provided by said baffles being arranged to produce a serpentine path through which material and air move through said drum;

a plurality of longitudinally extending, circumferentially-spaced ribs being provided around the inner circumference of the drum entrapping between consecutive ribs material being composted for the purpose of retaining inoculant and insulating the drum against both thermal loss and the corrosive effects of the composting process;

and introducing air into said drum in counter-flow relation to movement of material through the drum whereby waste material is converted into compost.

4. The method of converting organic waste material into compost, which comprises:

introducing organic waste material into a horizontally-disposed rotating drum;, a plurality of baffles being provided within said drum in spaced relation along and perpendicular to the longitudinal axis of the drum, each baffle having a cross-sectional area ranging from approximately 60 to 70% of the cross-sectional area of the drum;

the openings provided by said baffles being arranged to produce a serpentine path through which material and air move through said drum;

a plurality of longitudinally extending, circumferentially-spaced ribs being provided around the inner circumference of the drum entrapping between consecutive ribs material being composted thereby to retain inoculant and insulate the drum against both thermal loss and the corrosive effects of the composting process;

and introducing air into said drum in counter-flow relation to movement of material through the drum whereby waste material is converted into compost.

5. The method of converting organic waste material into compost as set forth in claim 4 wherein the cross sectional area of one or more baffles is adjustable to obstruct between from 60% to 100% of the cross sectional area of the drum.

* * * * *